United States Patent
Austen et al.

(10) Patent No.: US 10,245,066 B2
(45) Date of Patent: *Apr. 2, 2019

(54) METHOD AND APPARATUS FOR DISCONTINUOUS DERMABRASION

(71) Applicant: The General Hospital Corporation, Boston, MA (US)

(72) Inventors: William G. Austen, Weston, MA (US); Dieter Manstein, Coral Gables, FL (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/927,756

(22) Filed: Mar. 21, 2018

(65) Prior Publication Data
US 2018/0206875 A1 Jul. 26, 2018

Related U.S. Application Data

(63) Continuation of application No. 15/393,001, filed on Dec. 28, 2016, which is a continuation of application (Continued)

(51) Int. Cl.
*A61B 17/54* (2006.01)
*A61B 17/3205* (2006.01)
(Continued)

(52) U.S. Cl.
CPC .......... *A61B 17/3205* (2013.01); *A61B 17/54* (2013.01); *A61B 17/32* (2013.01);
(Continued)

(58) Field of Classification Search
CPC .......... A61B 2017/00761; A61B 2017/320004; A61B 2017/320008; A61B 2017/320012; A61B 17/54; A61B 17/3205
(Continued)

(56) References Cited

U.S. PATENT DOCUMENTS 3,214,869 A * 11/1965 Stryker .................. A61B 17/32
30/124
4,865,026 A 9/1989 Barrett
(Continued)

FOREIGN PATENT DOCUMENTS

EP 0027974 A1 5/1981
EP 1224949 A1 7/2002
(Continued)

OTHER PUBLICATIONS

Bedi et al., "The effects of pulse energy variations on the dimensions of microscopic thermal treatment zones in nonablative fractional resurfacing," Lasers Surg Med. 39(2):145-55 (2007).
(Continued)

*Primary Examiner* — David C Eastwood
(74) *Attorney, Agent, or Firm* — Quarles & Brady LLP

(57) ABSTRACT

Exemplary embodiments of method and apparatus are provided for resurfacing of skin that includes formation of a plurality of small holes, e.g., having widths less than about 1 mm or 0.5 mm. For example, such small holes can be produced using a mechanical apparatus that includes one or more abrading elements provided at the end of one or more rotating shafts, thus avoiding generation of thermal damage as occurs with conventional laser resurfacing procedures and devices. The holes thus formed can be well-tolerated by the skin, and may exhibit shorter healing times and less swelling than conventional resurfacing procedures. The fractional surface coverage of the holes can be between about 0.1 and 0.7, or between about 0.2 and 0.5. The method and apparatus can produce cosmetic improvements in the skin appearance by eliciting a healing response.

29 Claims, 2 Drawing Sheets

Related U.S. Application Data

No. 13/982,070, filed as application No. PCT/US2012/022987 on Jan. 27, 2012, now Pat. No. 9,561,051.

(60) Provisional application No. 61/437,500, filed on Jan. 28, 2011.

(51) Int. Cl.
  *A61B 17/32* (2006.01)
  *A61B 17/00* (2006.01)

(52) U.S. Cl.
  CPC .............. *A61B 2017/00561* (2013.01); *A61B 2017/00761* (2013.01); *A61B 2017/320004* (2013.01); *A61B 2217/005* (2013.01)

(58) Field of Classification Search
  USPC .......................................................... 606/131
  See application file for complete search history.

(56) References Cited

U.S. PATENT DOCUMENTS

| | | | |
|---|---|---|---|
| 5,749,895 A | 5/1998 | Sawyer et al. | |
| 5,885,211 A | 3/1999 | Eppstein et al. | |
| 6,211,598 B1 | 4/2001 | Dhuler et al. | |
| 6,241,739 B1 | 6/2001 | Waldron | |
| 6,251,097 B1 | 6/2001 | Kline et al. | |
| 6,432,098 B1 | 8/2002 | Kline et al. | |
| 6,562,037 B2 | 5/2003 | Paton et al. | |
| 6,669,618 B2 | 12/2003 | Reising et al. | |
| 6,669,694 B2 | 12/2003 | Shadduck | |
| 6,733,496 B2 | 5/2004 | Sharkey et al. | |
| 6,893,388 B2 | 5/2005 | Reising et al. | |
| 6,936,039 B2 | 8/2005 | Kline et al. | |
| 7,073,510 B2 | 7/2006 | Redmond et al. | |
| 8,209,006 B2 | 6/2012 | Smith et al. | |
| 8,246,611 B2 | 8/2012 | Paithankar et al. | |
| 8,435,791 B2 | 5/2013 | Galun et al. | |
| 9,561,051 B2 * | 2/2017 | Austen .................. | A61B 17/54 |
| 2002/0169431 A1 | 11/2002 | Kline et al. | |
| 2003/0088220 A1 | 5/2003 | Molander et al. | |
| 2003/0119641 A1 | 6/2003 | Reising | |
| 2003/0233082 A1 | 12/2003 | Kline et al. | |
| 2004/0010268 A1 * | 1/2004 | Gabehart .............. | A61B 17/54 606/131 |
| 2004/0015139 A1 * | 1/2004 | La Bianco ............ | A61B 17/54 604/289 |
| 2004/0023771 A1 | 2/2004 | Reising et al. | |
| 2005/0130821 A1 | 6/2005 | Reising et al. | |
| 2005/0215970 A1 | 9/2005 | Kline et al. | |
| 2005/0215971 A1 | 9/2005 | Roe et al. | |
| 2005/0234419 A1 | 10/2005 | Kline et al. | |
| 2005/0283141 A1 | 12/2005 | Giovannoli | |
| 2006/0047234 A1 * | 3/2006 | Glucksman ......... | A45D 26/0004 601/87 |
| 2007/0239260 A1 | 10/2007 | Palanker et al. | |
| 2008/0009901 A1 | 1/2008 | Redmond et al. | |
| 2009/0312749 A1 | 12/2009 | Pini et al. | |
| 2011/0251602 A1 | 10/2011 | Anderson et al. | |
| 2011/0313429 A1 | 12/2011 | Anderson et al. | |
| 2012/0041430 A1 | 2/2012 | Anderson et al. | |
| 2012/0136387 A1 | 5/2012 | Redmond et al. | |
| 2012/0226214 A1 | 9/2012 | Gurtner et al. | |
| 2012/0226306 A1 | 9/2012 | Jackson et al. | |
| 2012/0253333 A1 | 10/2012 | Garden et al. | |
| 2012/0271320 A1 | 10/2012 | Hall et al. | |
| 2013/0045171 A1 | 2/2013 | Utecht et al. | |
| 2016/0095592 A1 | 4/2016 | Levinson et al. | |

FOREIGN PATENT DOCUMENTS

| | | | |
|---|---|---|---|
| EP | 1278061 B1 | 2/2011 | |
| EP | 2409727 A1 | 1/2012 | |
| FR | 2846221 B1 * | 7/2005 | ............ A61B 10/02 |
| WO | WO 1999029243 A1 | 6/1999 | |
| WO | WO 2007024038 A1 | 3/2007 | |
| WO | WO 2012052986 A2 | 4/2012 | |
| WO | WO 2012103483 A2 | 8/2012 | |
| WO | WO 2012103488 A1 | 8/2012 | |
| WO | WO 2012103492 A1 | 8/2012 | |
| WO | WO 2012119131 A1 | 9/2012 | |
| WO | WO 2012135828 A1 | 10/2012 | |
| WO | WO 2013013196 A1 | 1/2013 | |
| WO | WO 2013013199 A2 | 1/2013 | |
| WO | WO 2014179729 A1 | 11/2014 | |
| WO | WO 2015021434 A2 | 2/2015 | |

OTHER PUBLICATIONS

Cevc, "Drug delivery across the skin," Expert Opin Investig Drugs. 6(12):1887-937 (1997).
Chang, "An updated review of tyrosinase inhibitors," Int J Mol Sci. 10(6):2440-2475 (2009).
Czech et al., Pressure-sensitive adhesives for medical applications. Wide Spectra of Quality Control. Akyar, 309-332 (2011).
Dai et al., "Magnetically-responsive self assembled composites," Chem Soc Rev. 39(11):4057-66 (2010.).
De las Heras Alarcon et al., "Stimuli responsive polymers for biomedical applications," Chem Soc Rev. 34(3):276-85 (2005).
Dini et al., "Grasping leather plies by Bernoulli grippers," CIRP Ann Manuf Technol. 58(1):21-4 (2009).
Dujardin et al., "In vivo assessment of skin electroporation using square wave pulses," J Control Release. 79 (1-3):219-27 (2002).
Fernandes et al., "Micro-mechanical fractional skin rejuvenation," Plast Reconstr Surg. 130(5S-1):28 (2012).
Fernandes et al., "Micro-mechanical fractional skin rejuvenation," Plast Reconstr Surg. 131(2):216-23 (2013).
Galaev., "'Smart' polymers in biotechnology and medicine," Russ Chem Rev. 64(5):471-489 (2005).
Glogau, "Aesthetic and anatomic analysis of the aging skin," Semin Cutan Med Surg. 15(3):134-8 (1996).
Hale et al., "Optical constants of water in the 200-nm to 200-microm wavelength region," Appl Opt. 12(3):555-63 (1973).
Huang et al., "Shape memory materials," Material Today 13(7-8):54-61 (2010).
International Preliminary Report on Patentability for International Patent Application No. PCT/US2014/036638, dated Nov. 3, 2015 (7 pages).
International Preliminary Report on Patentability for International Patent Application No. PCT/US2014/050426, dated Feb. 9, 2016 (8 pages).
International Search Report and Written Opinion for International Patent Application No. PCT/US2014/036638, dated Oct. 2, 2014 (10 pages).
International Search Report and Written Opinion for International Patent Application No. PCT/US2014/050426, dated Feb. 4, 2015 (18 pages).
Kakasheva-Mazenkovska et al., "Variations of the histomorphological characteristics of human skin of different body regions in subjects of different age," Prilozi. 32(2):119-28 (2011).
Konermann et al., "Ultrasonographically guided needle biopsy of benign and malignant soft tissue and bone tumors," J Ultrasound Med. 19(7):465-71 (2000).
Lien et al., "A novel gripper for limp materials based on lateral Coanda ejectors," CIRP Ann Manuf Technol. 57(1):33-6 (2008).
Majid, "Microneedling therapy in atrophic facial scars: an objective assessment," J Cutan Aesthet Surg. 2(1):26-30 (2009).
Pliquett et al., "A propagating heat wave model of skin electroporation," J Theor Biol. 251(2):195-201 (2008).
Prausnitz et al., "Electroporation of mammalian skin: a mechanism to enhance transdermal drug delivery," Proc Natl Acad Sci U S A. 90(22):10504-8 (1993).

\* cited by examiner

METHOD AND APPARATUS FOR DISCONTINUOUS DERMABRASION

CROSS REFERENCE TO RELATED APPLICATIONS

The present application is a continuation of U.S. patent application Ser. No. 15/393,001 filed Dec. 28, 2016, which is a continuation of U.S. application Ser. No. 13/982,070 filed Feb. 20, 2014, which is a U.S. National Phase of PCT Application No. PCT/US12/22987 filed on Jan. 27, 2012, which claims priority from U.S. Provisional Patent Application Ser. No. 61/437,500 filed Jan. 28, 2011, the disclosures of which are incorporated herein by reference in their entirety.

FIELD OF THE INVENTION

The present invention relates to exemplary embodiments of methods and apparatus for generating a plurality of small damaged regions in biological tissue, e.g., in skin or the like.

BACKGROUND INFORMATION

Conventional dermabrasion devices and techniques generally involve removal of an entire surface layer of skin tissue using mechanical means (for example, a rotating diamond head). Such techniques can produce a rejuvenating effect on the skin, but they generally require an extended healing time (during which the skin appears red and irritated) and may be very painful.

Procedures and devices for generating fractional damage in tissue are gaining increased attention and usage. Fractional damage includes forming small regions of damage in tissue (e.g., ablation or thermal damage) that are surrounded by healthy tissue. The small size of the damaged regions and proximity of healthy tissue can facilitate rapid healing of the damaged regions, as well as other desirable effects such as tissue shrinkage. Present approaches for generating fractional damage typically involve the use of expensive and potentially dangerous lasers or other sources of intense optical energy to damaged tissue, and can also generate associated thermal damage in the tissue which may be undesirable.

Accordingly, there is a need for a relatively simple, inexpensive, and safe dermabrasion method and apparatus that can reduce or eliminate some of the undesirable side effects of conventional dermabrasion procedures.

SUMMARY OF EXEMPLARY EMBODIMENTS

The herein described exemplary embodiments pertain to cosmetic method and apparatus. Synergetic effects can arise from different combinations of the features and embodiments described herein, although all such combinations might not be described in detail. Further, all exemplary embodiments of the present invention concerning a method can be carried out with the order of the steps and/or procedures as described; nevertheless this has not to be the only and essential order of the steps and/or procedures of the exemplary method. All different orders and combinations of the method steps and/or procedures are herewith described.

The exemplary embodiments of the present invention describe simple, inexpensive, and safe methods and devices for a mechanical generation of a plurality of small regions of damage in biological tissue by abrading small discrete regions of the tissue. Such damaged regions can have a size that is, e.g., about 1 mm or less as measured in at least one direction along the tissue surface.

An exemplary apparatus can be provided that includes one or more shafts that are freely rotatable. For example, the shafts can be configured to pass through a substrate or housing, or otherwise rotatably coupled thereto. The shafts can further be translatable along the longitudinal axis of the shafts relative to the substrate or housing. The shafts can further be provided with an abrading element at the distal end thereof. The abrading elements can be configured to contact the tissue surface to abrade a plurality of small, discrete regions of tissue when the shafts are rotated and/or impacted against the surface of the tissue. A width or diameter of the abrading elements can be small, e.g., about 1 mm or less, for example, less than about 0.8 mm, or less than about 0.5 mm, e.g., between about 0.3 mm and about 0.5 mm. Such small sizes of the abrading elements can facilitate removal of small portions of tissue and generation of small regions of abraded damage, e.g., holes, in the tissue. The substrate and shafts can be arranged to control and/or limit the depth of penetration or contact of the abrading elements into the tissue when the substrate is placed on or proximal to the tissue surface.

The damaged regions can be holes or disrupted tissue that result from mechanically abrading portions of tissue, e.g., by contacting the rotating abrading elements with the tissue surface. Such damaged regions can be generated in regular patterns or arrays, in one or more rows, in random spatial distributions, or in other patterns. The fraction of tissue surface area covered by the damaged regions can be between about 0.1 and 0.7, or between about 0.2 and about 0.5. Larger or smaller areal coverages can be generated in further embodiments.

In a further exemplary embodiment, the exemplary apparatus can further include a vacuum conduit configured to pull the tissue surface to contact the abrading elements when the apparatus is placed on the tissue surface. Such a vacuum arrangement can also stretch the tissue surface to provide mechanical stabilization of the tissue during abrasion. Other exemplary techniques for mechanically stabilizing the tissue surface region may also be used with exemplary embodiments of the present invention.

It shall further be noted that the exemplary cosmetic method described herein is a safe and routine procedure, comparable to conventional dermabrasion procedures that can be practiced in beauty parlors or other settings. Further, the exemplary method described herein is likely even less invasive than conventional dermabrasion procedures, because a significant fraction of the epidermis remains undamaged, which can lead to reduced swelling, reduced risk of infection, and faster healing times. Moreover, the exemplary method can minimally invasive, does not present a substantial health risk, and does not require professional medical expertise to be performed. For example, no clinician is needed to perform the exemplary embodiments of the method described herein, and no risk, much less a health risk, is presented for a person being treated with said cosmetic method, as will become clear from the following description.

In a still further exemplary embodiment, the exemplary apparatus can include a reciprocating arrangement affixed to the one or more shafts and attached abrading elements. The reciprocating arrangement can include a motor or other actuator configured to repeatedly advance and withdraw the abrading elements onto the skin surface. The reciprocating arrangement can be provided in a housing that facilitates manipulation of the apparatus, e.g., placement of the apparatus on the tissue being treated and/or traversing the apparatus over the tissue. The housing can optionally be configured to stretch or otherwise stabilize the skin tissue proximal to the shafts and abrading elements, e.g., to reduce deformation of the tissue and/or improve accuracy of the placement of the abrading elements on the tissue. The reciprocating arrangement can include an actuator and controller. In further embodiments, the reciprocating arrangement can include a trigger mechanism and a spring arrangement or the like, which may be configured to contact the abrading elements onto the skin surface, e.g., with a particular or predetermined force or depth, and alternately withdraw them from the skin surface. The reciprocating arrangement can further include a translational controller configured to translate the shaft(s) and abrading element(s) over the tissue in at least one direction, and optionally in two orthogonal directions, to provide larger regions of treatment without translating the entire apparatus over the tissue surface.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present invention, in which.

Figure 1:
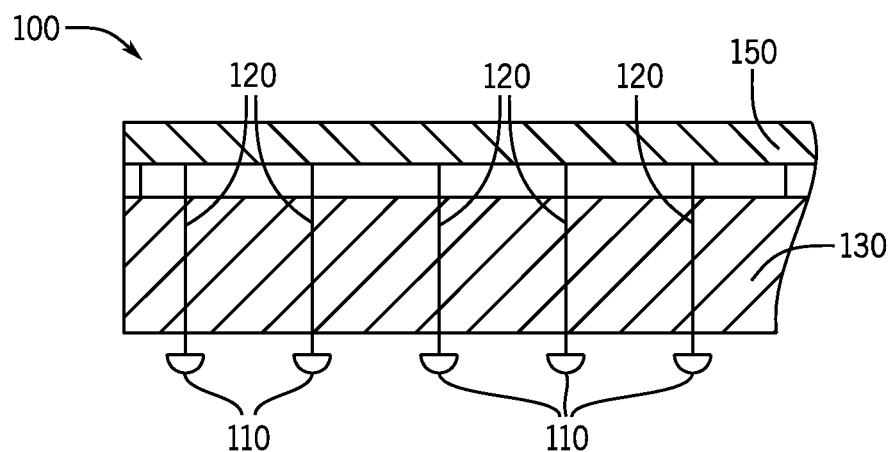
FIG. 1 is a schematic side view of an exemplary apparatus for mechanically generating fractional damage in tissue in accordance with exemplary embodiments of the disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular exemplary embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

According to exemplary embodiments of the present disclosure, method and apparatus can be provided for generating discontinuous damage in tissue such as, but not limited to, skin tissue. Such damage can be produced to any desired depth based on the configuration of the exemplary apparatus. For example, small areas of tissue damage (e.g., less than about 1 mm in width or diameter) can be created mechanically that extend to any desired depth within the skin, for example, down to the dermal/epidermal junction or just below it. In further exemplary embodiments, the depth of the abraded and removed tissue can extend into the dermis.

A side cross-sectional view of an exemplary apparatus 100 for generating discontinuous damage in a tissue is shown in FIG. 1. The exemplary apparatus 100 can include a plurality of shafts 120 that can be rotatably coupled to a substrate 130. For example, the shafts 120 can pass at least partially through holes provided in the substrate 130, or be coupled to rotational bearings affixed to the substrate 130, etc. The substrate 130 can be formed as part of a housing, or be affixed to a housing. The shafts 120 can be substantially parallel to one another, and can be rotatable around and/or slidable along their longitudinal axes relative to the substrate 130. An abrading element 110 can be affixed to the distal end of each shaft 120. In certain embodiments, the abrading elements 110 can be formed as a shaped portion of the distal ends of the shafts 120.

The abrading elements 110 can preferably be small, for example, having a width or diameter that is less than about 1 mm, or less than about 0.8 mm. In further exemplary embodiments, the width of the abrading element 110 can be less than about 0.5 mm, for example, between about 0.3 mm and about 0.5 mm. The shape of the abrading elements 110 can be spherical, cylindrical, conical, or the like. Each abrading element 110 can include an abrasive medium provided over at least a part of the outer surface. The abrasive medium can include, for example, a diamond or metallic powder, carbide particles, or the like. In further exemplary embodiments, the abrasive medium can be a pattern or plurality of recesses, grooves, protrusions, or the like formed in the abrading elements 110. Such exemplary geometric features can be etched in silicon or another material that forms the abrading element 110, for example, in the shape of a conventional pineapple burr arrangement, etc.

The proximal end of the shafts 120 can be coupled to a drive arrangement 150. The drive arrangement 150 can optionally be configured to controllably rotate the shafts 120, at either low or high rotational speeds. For example, the drive arrangement 150 can include a small fan or turbine affixed to the proximal end of each of the shafts 120. A rapid flow of air or another gas, or a plurality of bursts or pulses of such gas, can be directed over the fans or turbines to drive a rapid rotation of the shafts 120 and of the abrading elements 110 affixed thereto. In certain exemplary embodiments, the rotation can be small each time the abrading elements 110 contact the skin, e.g., they can be limited to just a few full (360 degree) rotations, or one full rotation or less, to limit the amount of abrasion that is generated on the skin surface. The amount of rotation can be selected, for example, based on the structure and abrasiveness of the abrasive elements 110 used.

Alternatively, the drive arrangement 150 can include a gear affixed to the proximal portion of each shaft 120. The drive arrangement 150 can further include a conventional rack-and-pinion mechanism or the like, in which a toothed edge of a flat rod can engage a plurality of the gears that are attached to shafts 120 that are aligned in a row through the substrate 130. The shafts 120 can then be controllably rotated by rapidly moving the flat rod back and forth, converting the translational motion of the rod to rotational movement of the shafts 120 affixed to the gears. Other gear arrangements can be provided in the drive arrangement 150 to controllably rotate one or more of the shafts 120.

Figure 2:
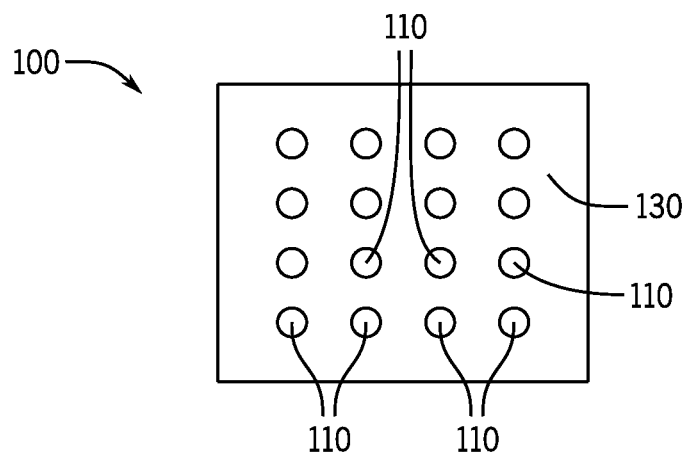
FIG. 2 is a frontal view of the exemplary apparatus shown in FIG. 1.

A bottom view of the exemplary apparatus 100 is shown in FIG. 2. The abrading elements 110—and shafts 120 they are affixed to—can be arranged in a square or rectangular pattern, as shown in FIG. 2. Alternatively, the rows of abrading elements 110 can be offset or staggered to form a triangular pattern or other spatial pattern. Other arrangements of the abrading elements 110 can also be used, such as a random distribution of the abrading elements 110 and the corresponding shafts 120 on the substrate 130. If the shafts 120 are not arranged in rows, it can be preferable to use a turbine mechanism or the like for the drive arrangement 150, rather than a rack-and-pinion mechanism. The shape of the bottom of the substrate 130 shown in FIG. 2 is substantially square. Other shapes and sizes of the substrate 130 can also be used, and different numbers of abrading elements 110 (and corresponding shafts 120) can be provided.

The lower portion of the exemplary apparatus 100 can be pressed onto a tissue surface, and the abrading elements 110 can be rotated at high speeds so they abrade tissue at the skin surface and optionally penetrate some depth into the tissue. This exemplary procedure can form a plurality of small, discrete abraded regions or holes in the tissue. The holes can have a spacing substantially similar to the spacing of the shafts 120 in the apparatus 100. In certain exemplary embodiments, the abrading elements 110 can be configured to protrude only a small distance from the bottom surface of the substrate 130, e.g. to limit the depth at which tissue is abraded when the apparatus 100 is placed on the tissue to be treated. For example, the distal ends of the abrading elements 110 can protrude about 3 mm from the bottom surface of the substrate 130, such that the abraded depth may extend into the upper epidermal layer in skin tissue. Smaller protrusion distances may be used, e.g., less than about 2 mm, or less than about 1 mm, to reduce or limit the depth of skin tissue that is abraded to the epidermal layer or just below the dermal/epidermal junction.

The plurality of holes or abraded regions abrasively formed by the exemplary apparatus 100 can represent regions of damaged tissue that may elucidate a healing response in the tissue. This behavior can be qualitatively similar to the effects produced using conventional laser-based fractional resurfacing techniques and systems. The size of the holes can be determined by the size of the abrading elements 110 and the depth to which they are introduced into the tissue. The hole sizes can be slightly larger than the diameter of the abrading elements 110 based on local mechanical disruption of the tissue. In conventional fractional resurfacing techniques, the diameter or width of the damaged tissue regions may be less than about 1 mm, or less than about 0.5 mm, and can also generate thermal damage zones around these damaged regions. The exemplary apparatus 100 can be configured to form holes or abraded regions having similar dimensions, with little or no adjacent thermal damage zone because the damage is generated mechanically. Larger or smaller holes can be formed in certain tissues to achieve particular healing responses or other physical or biological responses. These holes can be formed discretely such that each hole is substantially surrounded by healthy, undamaged tissue. The presence of healthy tissue proximal to the holes or abraded regions can facilitate a more rapid healing of the skin while producing cosmetically desirable effects, such as wrinkle reduction and/or collagen formation.

The surface or areal fraction of tissue damage can be determined by the diameters and spacings of the abrading elements 110 provided on the shafts 120 connected to the substrate 130. For example, the fraction of the tissue surface covered by abraded holes can be as small as about 0.1 or large as about 0.7. In general, areal fractions of the holes thus formed can be between about 0.2 and 0.5 to achieve a sufficient desirable healing response while being well-tolerated, so that healing times are relatively short. Smaller areal coverages can also be generated for certain areas of skin, e.g., skin that may be more sensitive to larger densities of damage.

The depth of the holes formed by abrasive removal of tissue can correspond approximately to the distance that the abrading elements 110 protrude from a lower surface of the substrate 130. For example, the abrading elements 110 can extend about 1 mm below the lower surface of the substrate 130. This length can facilitate abrasive formation of holes that extend to a depth that is approximately midway through the dermal layer. Shallower or deeper holes can be formed by altering or adjusting the protrusion distances of the abrading elements 110 from the bottom of the substrate 130. These exemplary distances and corresponding hole depths can be selected based on the characteristics of the tissue being treated and the desired effects to be achieved.

Figure 3:
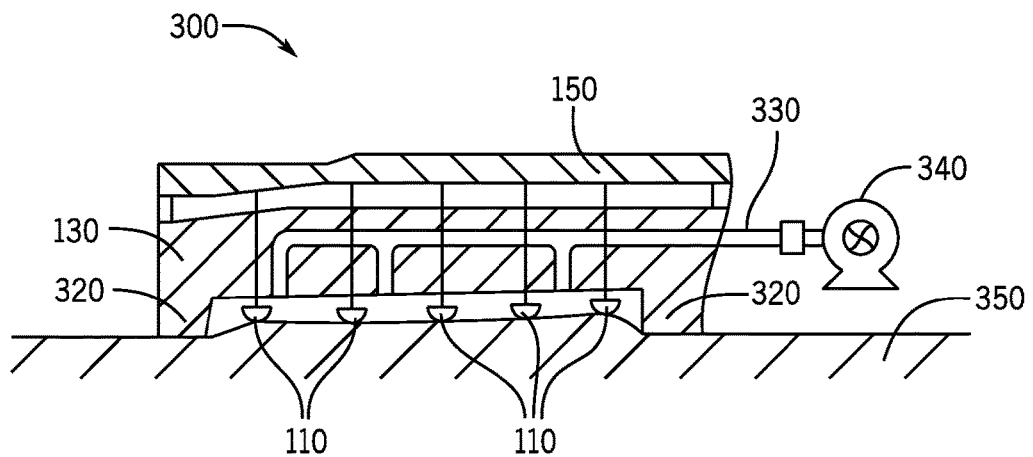
FIG. 3 is a schematic side view of a second exemplary apparatus for mechanically generating discontinuous dermabrasion in tissue in accordance with further exemplary embodiments of the disclosure.

A side view of a further exemplary apparatus 300 for generating abrasive discontinuous damage in tissue according to another exemplary embodiment is shown in FIG. 3. This exemplary apparatus 300 can be similar to the exemplary apparatus 100 shown in FIG. 1. The exemplary apparatus 300 further includes a lip or rim 320 around the lower perimeter of the substrate 130. A vacuum conduit 330 can be provided in the substrate that includes one or more openings along the bottom of the substrate 130. The apparatus 300 can be placed onto the surface of a tissue 350, such that the lower rim 320 rests on the tissue 350.

A vacuum source 340 (e.g., a source of a fluid at a pressure lower than atmospheric or ambient pressure) can be coupled to the vacuum conduit 330, such that the tissue surface 350 is pulled up towards the abrading elements 110. The fluid can be a gas, e.g. air or nitrogen or the like. Alternatively, the fluid can be a liquid such as, e.g., water or a saline solution. The vacuum source 340 can be, for example, a pump, a piston arrangement, a reservoir or enclosure provided with a valve arrangement, or the like. By controlling the vacuum source 340, the tissue 350 can be brought into contact with the abrading elements 110 to abrade a plurality of small holes in the tissue 350. In certain exemplary embodiments, the drive arrangement 150 can optionally be activated to spin the abrading elements 110, e.g., at high rotational speeds. The vacuum source 340 and the vacuum conduit 330 can also facilitate removal of abraded tissue debris when forming the small holes. Further, the exemplary configuration of the substrate 130, rim 320 and optionally the vacuum conduit 330 can stretch the tissue 350, which can provide mechanical stabilization of the tissue 350 while it is being abraded.

Figure 4:
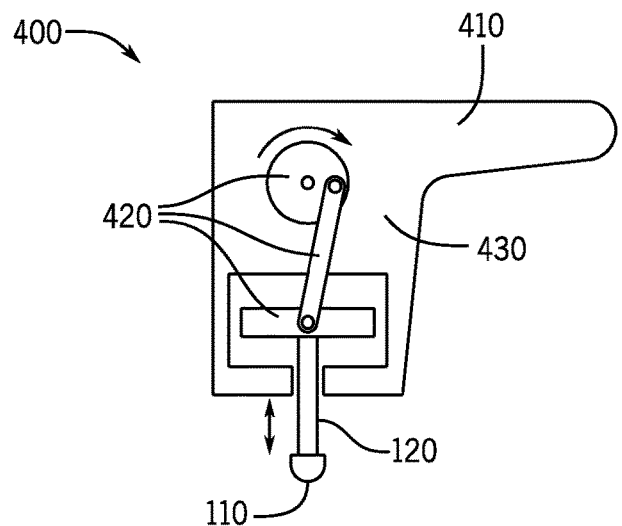
FIG. 4 is a schematic side view of a third exemplary apparatus for mechanically generating discontinuous dermabrasion in tissue in accordance with still further exemplary embodiments of the disclosure.

An exemplary apparatus 400 in accordance with further exemplary embodiments of the present invention is shown in FIG. 4. The exemplary apparatus 400 can include one or more shafts 120 affixed or coupled to a reciprocating arrangement 420, which may be provided at least partially within a housing 430. The shafts 120 can be rotatable, as described herein above, or non-rotating. An abrading element 110 can be provided at the distal end of the shafts 120. The housing 430 can also include a handle 410 to facilitate manipulation of the exemplary apparatus 400. The reciprocating arrangement 420 can be configured to displace the shaft(s) 120 back and forth along a direction that can be substantially parallel to the axis of the shaft 120. For example, the reciprocating arrangement 420 can be powered by a motor or the like, and controlled by a switch that can turn the reciprocating arrangement 420 on and off, and may further control the reciprocating frequency and/or protrusion distance of the abrading element 110 below the lower surface of the housing 430.

The exemplary apparatus 400 can be traversed over a region of tissue to be treated such that the one or more abrading elements 110 provided at the distal ends of the shafts 120 form a plurality of discrete abraded regions or holes in the tissue 350 as described herein. The exemplary depth of the holes or abraded regions in the tissue 350 can be determined by the configuration of the reciprocating arrangement 420. The exemplary spacing of such holes in the tissue 350 can be determined, e.g., by the reciprocating frequency and/or the translational speed of the apparatus 400 over the tissue surface. For example, the exemplary apparatus 400 can include a speed and/or position sensing arrangement that can be provided in communication with the reciprocating arrangement 420 to generate a particular spacing and/or areal fraction of holes.

According to yet further exemplary embodiments, the housing 430 can be configured to stretch skin or other tissue when the exemplary apparatus 400 is placed on the tissue to be treated. Such stretching can facilitate mechanical stabilization of the tissue, e.g., to reduce or avoid deformation of the tissue 350 while the abrading elements 110 are in contact with the tissue 350. Such stretching of the tissue 350 can also reduce the effective size of the holes or discrete abraded regions of damage formed by the apparatus when the tissue 350 is allowed to relax after treatment. Alternatively, the surface of the tissue 350 to be treated can be stretched or stabilized using other exemplary techniques prior to and/or during treatment of the region in accordance with any of the exemplary embodiments described herein.

In still a further exemplary embodiment, the reciprocating arrangement 420 can further include a translational mechanism configured to translate the one or more shafts 120 over the tissue surface in one or two orthogonal directions. For example, the reciprocating arrangement 420 can be configured to translate the one or more shafts 120 over a portion of the tissue 350 while the apparatus 400 is held stationary with respect to the tissue surface. In one exemplary embodiment, the reciprocating arrangement 420 can be configured to translate the one or more shafts 120 along a single direction to form one or more rows of holes or abraded regions using the abrading elements 110 provided at the distal ends of the shafts 120. The exemplary apparatus 400 can optionally be translated over the tissue surface after such rows are formed, e.g., in a direction that is not parallel to the row, to generate a plurality of such holes or abraded regions over a larger area of the tissue.

According to yet another embodiment, the reciprocating arrangement 420 can include a spring-loaded mechanism. For example, a trigger mechanism and spring arrangement or other tensile mechanism can be coupled to the one or more shafts 120 within the housing 430. Activating the trigger can extend the shafts 120 such that the abrading elements 110 protrude a particular distance from the lower portion of the housing 430. When the trigger is released, the spring arrangement can retract the ends of the shafts 120 and associated abrading elements away from the skin surface when the lower portion of the housing 430 is placed against the tissue surface to be treated. The housing 430 and reciprocating arrangement 420 can be configured such that the abrading elements 110 protrude a preselected distance from a lower surface of the housing 430 when the trigger is fully engaged, e.g., to limit the depth of holes formed by the abrading elements 110. This exemplary embodiment of the reciprocating arrangement 420 can thereby facilitate repeated contact of the abrading elements 110 against the skin surface with a known force and/or at a predetermined impact depth to achieve a desirable amount of abrading tissue damage with each contact. Other configurations of the reciprocating arrangement 420 can also be used in embodiments of the present invention to achieve similar effects.

In still further exemplary embodiments of the present disclosure, any of the exemplary apparatuses described herein can be configured to generate a plurality of holes or abraded regions in any of a variety of spatial distributions in the tissue being treated. For example, the holes or discrete abraded regions can be formed as one or more rows, a regular two-dimensional pattern, a random distribution, or the like. Such patterns or spatial distributions of holes can be generated based on, e.g., the configuration of the one or more needles 120 provided, the properties of the reciprocating arrangement 420, and/or the rate of translation of the exemplary apparatus 400 over the tissue surface.

For example, a topical anesthetic and/or cooling/freezing can be applied to the tissue surface before forming the abraded holes to reduce any sensation of pain or discomfort during the procedure. Further, partially freezing the tissue can reduce the amount of tissue tearing and form smoother holes. Antibiotics or other therapeutic substances can also be applied topically after the holes have been formed to promote healing, skin tightening, and/or other desirable effects.

The foregoing merely illustrates the principles of the present invention. Other variations to the disclosed embodiments can be understood and effected by those skilled in the art in practising the claimed invention from a study of the drawings, the disclosure, and the appended claims. In the claims, the word "comprising" does not exclude other elements or steps and the indefinite article "a" or "an" does not exclude a plurality. The mere fact that certain measures are recited in mutually different dependent claims does not indicate that a combination of these measures cannot be used advantageously. Any reference signs in the claims should not be construed as limiting the scope of the claims. Various modifications and alterations to the described embodiments will be apparent to those skilled in the art in view of the teachings herein. It will thus be appreciated that those skilled in the art will be able to devise numerous techniques which, although not explicitly described herein, embody the principles of the present invention and are thus within the spirit and scope of the present invention. All references cited herein are incorporated herein by reference in their entireties.

What is claimed is:

1. An apparatus for cosmetic resurfacing of a skin tissue, comprising:
    a housing;
    a plurality of shafts, each of which has a corresponding longitudinal axis and a skin abrading element at a distal end thereof, wherein the skin abrading element is configured to contact a surface of the skin tissue to generate holes in the skin tissue by removing portions of the skin tissue while leaving surrounding tissue healthy;
    a shaft drive arrangement configured to rotate each shaft of the plurality of shafts around the corresponding longitudinal axis of each of the plurality of shafts; and a low-pressure source configured to pull the tissue up toward the skin abrading elements or to facilitate removal of the abraded tissue.

2. The apparatus of claim 1, wherein the width of the skin abrading element is about 1.0 mm or less.

3. The apparatus of claim 1, wherein the width of the skin abrading element is about 0.5 mm or less.

4. The apparatus of claim 1, further comprising a substrate affixed to or integrated into the housing, wherein the shafts are rotatably coupled to the substrate.

5. The apparatus of claim 4, wherein the shafts protrude from a bottom of the substrate, and wherein a protrusion distance of the shafts from the bottom of the substrate is adjustable.

6. The apparatus of claim 1, further comprising a shaft reciprocating arrangement configured to translate the shafts in a direction substantially along the longitudinal axis of the shafts.

7. The apparatus of claim 6, wherein the shaft reciprocating arrangement comprises an actuator and a control arrangement.

8. The apparatus of claim 6, wherein the shaft reciprocating arrangement is configured to control the protrusion distance of the shafts from a lower surface of the housing.

9. The apparatus of claim 6, wherein the shaft reciprocating arrangement is configured to bring the skin abrading element in contact with the surface of the skin tissue with a predetermined force or depth.

10. The apparatus of claim 6, wherein the shaft reciprocating arrangement is enclosed in the housing.

11. The apparatus of claim 1, further comprising a conduit configured to facilitate contact between a surface of the skin tissue and the skin abrading element when the conduit is placed in communication with the low-pressure source.

12. The apparatus of claim 1, wherein the shape of the skin abrading element is spherical, cylindrical, or conical.

13. The apparatus of claim 1, wherein the skin abrading element comprises an abrasive medium.

14. The apparatus of claim 1, wherein an areal fraction of the skin tissue covered by the holes generated by the apparatus is between 0.1 and 0.7.

15. The apparatus of claim 1, wherein an areal fraction of the skin tissue covered by the holes generated by the apparatus is 0.1.

16. The apparatus of claim 1, wherein the depth of the holes generated by the skin abrading element in the skin tissue is (i) into the upper epidermal layer, (ii) at the dermal/epidermal junction, or (iii) below the dermal/epidermal junction.

17. The apparatus of claim 1, wherein the plurality of shafts are arranged in an array comprising one or more rows, or in a random spatial distribution, so that operation of the device generates a corresponding pattern of holes in the tissue by removing portions of the skin tissue.

18. The apparatus of claim 1, wherein the low-pressure source is a vacuum pump or a piston.

19. The apparatus of claim 1, wherein the housing is configured to stretch and/or stabilize the skin tissue proximal to the at least one shaft, to reduce deformation of the skin tissue, and/or to improve accuracy of the insertion of the at least one shaft into the skin tissue.

20. The apparatus of claim 1, wherein the shaft drive arrangement comprises a fan, a turbine, and/or a rack-and-pinion mechanism comprising one or more gears.

21. The apparatus of claim 1, wherein the shaft drive arrangement comprises a gear arrangement to controllably rotate the plurality of shafts.

22. The apparatus of claim 1, wherein the shaft drive arrangement comprises a gear affixed to a proximal portion of each shaft.

23. A method for resurfacing skin tissue, comprising: producing a plurality of holes in the skin tissue using the apparatus of claim 1, wherein each hole is produced by removing a portion of the skin tissue, and wherein a surface area fraction of the removed portions of the skin tissue is between 0.1 and 0.7.

24. The method of claim 23, wherein the width of each hole is less than about 1.0 mm.

25. The method of claim 23, wherein a surface area fraction of the removed portions of the skin tissue is about 0.1.

26. The method of claim 23, wherein at least one of the holes extends to a depth of (i) the upper epidermal layer, (ii) the dermal/epidermal junction, or (iii) below the dermal/epidermal junction.

27. The method of claim 23, wherein the width of each hole is between about 0.3 mm and about 0.5 mm.

28. The method of claim 23, wherein an array in one or more rows or in a random spatial distribution is generated by the plurality of holes.

29. An apparatus for cosmetic resurfacing of a skin tissue, comprising:
a housing;
a plurality of shafts, each of which has a corresponding longitudinal axis and a skin abrading element at a distal end thereof, wherein the skin abrading element is configured to contact a surface of the skin tissue to generate holes in the skin tissue by removing portions of the skin tissue while leaving surrounding tissue healthy;
a shaft drive arrangement configured to rotate each shaft of the plurality of shafts around the corresponding longitudinal axis of each of the plurality of shafts; and
a shaft reciprocating arrangement configured to translate the shafts in a direction substantially along the longitudinal axis of the shafts, wherein the shaft reciprocating arrangement is configured to control the protrusion distance of the shafts from a lower surface of the housing.

* * * * *